(12) United States Patent
Brockmeier et al.

(10) Patent No.: US 7,914,496 B2
(45) Date of Patent: Mar. 29, 2011

(54) ACCESS ASSEMBLY WITH RIBBED SEAL

(75) Inventors: Oivind Brockmeier, Middlesex, MA (US); Jared Alden Judson, Topsfield, MA (US); Kenneth Allen Focht, Needham, MA (US)

(73) Assignee: Tyco Healthcare Group LP, North Haven, CT (US)

( * ) Notice: Subject to any disclaimer, the term of this patent is extended or adjusted under 35 U.S.C. 154(b) by 39 days.

(21) Appl. No.: 12/124,654

(22) Filed: May 21, 2008

(65) Prior Publication Data
US 2008/0294113 A1 Nov. 27, 2008

Related U.S. Application Data

(60) Provisional application No. 60/931,253, filed on May 22, 2007.

(51) Int. Cl.
*A61M 5/178* (2006.01)
(52) U.S. Cl. .............................. 604/167.06; 604/167.01
(58) Field of Classification Search ............ 604/167.04, 604/167.06, 167.01, 164.02, 256
See application file for complete search history.

(56) References Cited

U.S. PATENT DOCUMENTS

| | | | |
|---|---|---|---|
| 4,809,679 A | 3/1989 | Shimonaka et al. |
| 4,842,591 A | 6/1989 | Luther |
| 5,085,645 A | 2/1992 | Purdy |
| 5,209,737 A | 5/1993 | Ritchart et al. |
| 5,295,657 A | 3/1994 | Atkinson |
| 5,295,658 A | 3/1994 | Atkinson et al. |
| 5,312,363 A | 5/1994 | Ryan et al. |
| 5,342,315 A | 8/1994 | Rowe et al. |
| 5,496,280 A | 3/1996 | Vandenbroek et al. |
| 5,545,142 A | 8/1996 | Stephens et al. |
| 5,549,565 A | 8/1996 | Ryan et al. |
| 5,591,137 A | 1/1997 | Stevens |

(Continued)

FOREIGN PATENT DOCUMENTS

EP 0 784 961 A1 7/1997

(Continued)

OTHER PUBLICATIONS

European Search Report for corresponding EP 08251757 date of mailing is Sep. 25, 2008 (3 pages).

*Primary Examiner* — Nicholas D Lucchesi
*Assistant Examiner* — Brooke M Matney

(57) ABSTRACT

A ribbed seal for use in endoscopic surgery is intended to be incorporated into a cannula assembly to limit the escape of insufflation gasses from a body cavity by forming a fluid-tight seal around an instrument inserted through the cannula assembly. The ribbed seal includes a relatively flat, disk shaped elastomeric overmold portion having a central aperture sized slightly smaller than the instrument such that the aperture must expand to accommodate the instrument. Molded together with the elastomeric overmold is an array of slender ribs disposed about the aperture. The ribs are designed to be relatively flexible under lateral loads. This allows the seal to bend easily as the surgical instrument is inserted through the aperture thereby maintaining a low insertion and glide force. On the other hand, the ribs are designed to be relatively rigid when loaded axially. This rigidity provides robust radial support for the instrument inserted through the center of the array of ribs. The seal performs a centering function for the instrument due to its combined elasticity and stiffness. Finally, the seal also allows for an instrument to be removed easily while maintaining the required atmospheric integrity.

19 Claims, 4 Drawing Sheets

U.S. PATENT DOCUMENTS

| | | | |
|---|---|---|---|
| 5,603,702 | A | 2/1997 | Smith et al. |
| 5,628,732 | A | 5/1997 | Antoon, Jr. et al. |
| 5,685,854 | A | 11/1997 | Green et al. |
| 5,693,025 | A | 12/1997 | Stevens |
| 5,727,770 | A | 3/1998 | Dennis |
| 5,871,471 | A | 2/1999 | Ryan et al. |
| 5,871,474 | A | 2/1999 | Hermann et al. |
| 5,997,515 | A | 12/1999 | de la Torre et al. |
| 6,053,861 | A | 4/2000 | Grossi |
| 6,093,176 | A | 7/2000 | Dennis |
| 6,099,505 | A | 8/2000 | Ryan et al. |
| 6,238,373 | B1 | 5/2001 | de la Torre et al. |
| 6,258,065 | B1 * | 7/2001 | Dennis et al. ............ 604/167.03 |
| 6,280,417 | B1 | 8/2001 | Bohannon et al. |
| 6,486,292 | B2 | 11/2002 | You et al. |
| 6,632,200 | B2 | 10/2003 | Guo et al. |
| 6,726,663 | B1 | 4/2004 | Dennis |
| 6,863,661 | B2 | 3/2005 | Carrillo, Jr. et al. |
| 7,112,185 | B2 | 9/2006 | Hart et al. |
| 7,114,701 | B2 | 10/2006 | Peppel |
| 2002/0010425 | A1 | 1/2002 | Guo et al. |
| 2004/0230161 | A1 | 11/2004 | Zeiner |
| 2005/0065475 | A1 | 3/2005 | Hart et al. |
| 2006/0224164 | A1 | 10/2006 | Hart et al. |
| 2007/0027453 | A1 | 2/2007 | Hart et al. |
| 2007/0270756 | A1 | 11/2007 | Peppel et al. |
| 2008/0033363 | A1 | 2/2008 | Haberland et al. |
| 2008/0300455 | A1 | 12/2008 | Smith |

FOREIGN PATENT DOCUMENTS

| | | |
|---|---|---|
| EP | 1348386 A | 10/2003 |
| EP | 1 520 537 A1 | 4/2005 |
| EP | 1671596 A | 6/2006 |
| EP | 1 716 813 A1 | 11/2006 |

* cited by examiner

ACCESS ASSEMBLY WITH RIBBED SEAL

CROSS REFERENCE TO RELATED APPLICATION

The present application claims the benefit of and priority to U.S. Provisional Application Ser. No. 60/931,253 filed on May 22, 2007, the entire contents of which are incorporated herein by reference.

BACKGROUND

1. Technical Field

The present disclosure relates generally to a seal for use in endoscopic surgery adapted to maintain a fluid-tight connection about an instrument inserted through a cannula. In particular, the disclosure relates to a seal member having elasticity and rigidity characteristics which facilitate its effective use.

2. Background of Related Art

Minimally invasive surgical procedures are performed throughout the body and generally rely on obtaining access to an internal surgical site through a small incision made in the skin of a patient. A cannula is a narrow tube, typically 5 to 13 mm in diameter, which is partially inserted into the small incision in the skin to hold the incision open. The cannula provides a portal or conduit between the surgical site and the exterior of the patient's body through which a surgeon may introduce the various surgical instruments required by the desired procedures.

A cannula assembly typically includes components adapted to maintain a seal across its opening at all times, i.e., prior to, during and subsequent to the introduction or removal of a surgical instrument. The need for a fluid-tight seal is apparent when considering laparoscopic procedures in which an insufflation gas, usually carbon dioxide, is introduced into the patient's abdomen under a slight pressure to separate the abdominal wall from the vital organs. The inflation of the abdominal cavity provides a space where a surgeon may introduce viewing equipment or maneuver instruments into position. The fluid-tight seal is needed in this context to prevent the escape of insufflation gas to maintain this viewing and working space.

A dual seal system may be used to prevent the escape of insufflation gas. A first type of "cannula" seal serves to provide the seal in the absence of an instrument, but is usually defeated as soon as an instrument is introduced. A second type of "instrument seal" is capable of making a fluid-tight connection with the instrument, but is usually defeated as soon as the instrument is withdrawn. Placing an instrument seal proximally in relation to a cannula seal will allow the two seals to cooperate to seal the cannula at all times. A flapper valve may be used as a cannula seal of the first type. This type of seal has a flap which normally closes the passageway through a cannula, but is forced to pivot open by the distal end of an instrument. The flap may be biased by a spring to close once the surgeon withdraws the instrument. Another type of self-closing valve used for this purpose is an elastomeric duckbill valve. This type of valve closes with the assistance of the positive pressure inside an insufflated body cavity which forces the distal faces of the duckbill into sealing abutment with each other. As discussed above, a flapper valve, a duckbill valve or other type of cannula seal typically will not prevent fluid losses once an instrument is in place within the cannula. Accordingly, an instrument seal of the second type is provided. A simple type of conventional instrument seal includes a relatively flat elastomeric member with an aperture sized slightly smaller than the instrument to be introduced. The elastomeric member stretches and bends to expand the aperture to accommodate the instrument.

An effective instrument seal will exhibit several characteristics, a few of which are listed here. First, of course, is the ability to maintain a fluid-tight connection with a surgical instrument as the instrument is being used. A surgeon will likely advance the instrument distally through the aperture of the instrument seal, manipulate the instrument with both radial and angular movements, and finally withdraw the instrument. Through all of this movement, the instrument seal must be flexible enough to allow the aperture to move and reshape itself appropriately to maintain the necessary fluid-tight connection. Second, it is important that the instrument seal not hinder the efforts of the surgeon in advancing and withdrawing the instrument. There is a friction force associated with moving the instrument while it is in contact with the aperture of the instrument seal. This friction force is sometimes called an insertion force or glide force and must be low enough such that manipulating the instrument is not awkward for the surgeon. Also, an effective instrument seal will provide radial support for an instrument. Adequate radial support will aid in stabilizing the instrument so a surgeon need not direct too much attention to holding the instrument in position while performing the surgical procedures. Additionally, it is important that the instrument seal have memory to return to its original shape and position after use. This feature can facilitate the insertion of subsequent instruments. Finally, because a single surgical procedure will often require many instruments dissimilar size, an effective instrument seal will be able to accommodate instruments having a wide range of sizes.

Design considerations intended to enhance some of these instrument seal characteristics may also enhance others. For example, features designed to give an instrument seal radial rigidity to provide radial support to an instrument are also likely to be helpful in providing an instrument seal with memory. On the other hand, many of these design considerations compete with one another. In particular, to provide an instrument seal with a sufficient closing force to maintain a fluid-tight connection with an instrument, an elastomeric member may be provided which has an increased cross sectional thickness about the aperture. The increased surface area in contact with the instrument will enhance the sealing characteristics, but at the same time will adversely affect the insertion and glide forces. An instrument seal designed to be extremely flexible in order to minimize insertion and glide forces may be ineffective in providing radial support to an instrument. Accordingly, an effective instrument seal is capable of balancing the competing design goals to allow for an effective fluid-tight seal to be maintained while not providing a difficult or awkward use.

SUMMARY

The present disclosure describes a seal mounted within a cannula assembly adapted to engage a surgical instrument to permit sealed entry of the instrument into an internal tissue site. The seal includes a first elastomeric member having a passageway for the instrument along a seal axis and a second member at least partially embedded within the first member to urge the instrument into general alignment with the seal axis. The second member includes an annular element and at least one rib extending inwardly from the annular element toward the seal axis.

In other embodiments, the seal may include a radial array of ribs extending inwardly from the annular element which may cooperate to urge the instrument into alignment with the seal axis. Furthermore, the seal may be a septum seal having a generally planar configuration with an aperture for passage of the instrument. The rib or ribs included on the seal may be tapered such that the width decreases toward the seal axis, or the rib or ribs may be generally diamond shaped such that the width decreases toward the annular element as well as toward the seal axis. Openings may be included on a rib to enhance its flexibility. The ribs may include a free end which is adjacent to the passageway through the first elastomeric member, and the free end may be substantially spaced from the passageway. An alternative rib shape involves a fork such that a first leg of the rib extends inwardly from the annular element and second and third legs extend inwardly from the first leg. The second and third legs of a forked rib may be spaced from one another and include portions which are generally parallel.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF PREFERRED EMBODIMENTS

Figure 1:
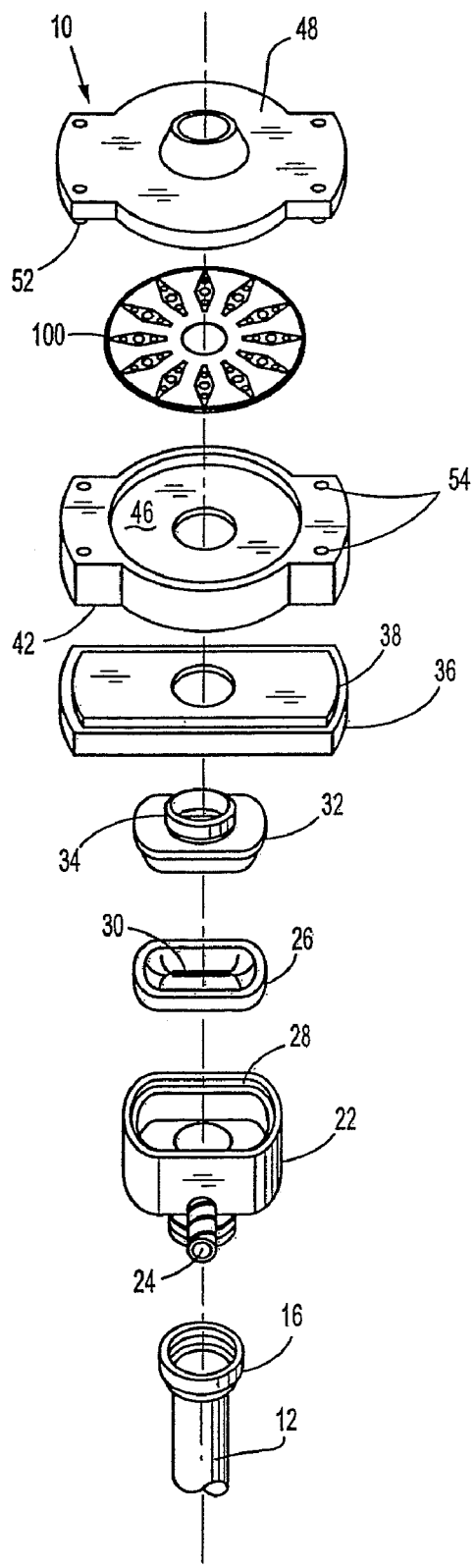
FIG. 1 is an exploded perspective view of a ribbed seal member incorporated into a cannula assembly.

The present disclosure contemplates the introduction into a person's body of all types of surgical instruments including clip appliers, graspers, dissectors, retractors, staplers, laser fibers, photographic devices, endoscopes and laparoscopes, tubes, and the like. All such objects are referred to herein generally as "instruments." In the drawings and in the description which follows, the term "proximal," as is traditional, will refer to the direction toward the operator or a relative position on the surgical device or instrument which is closer to the operator, while the term "distal" will refer to the direction away from the operator or relative position of the instrument which is further from the operator.

Referring initially to FIG. 1, the ribbed seal 100 of the present invention is shown as a component of cannula assembly 10. The distal end (not shown) of cannula 12 is intended to be inserted into a body cavity through a small cut made in the skin to provide a portal or conduit into the body cavity. Enlarged proximal portion 16 of cannula 12 may contain internal threads for attachment to external threads disposed on the distal end of lip seal body 22.

Lip seal body 22 includes port 24 through which an insufflation gas may be inserted and directed through cannula 12 into the body cavity. Lip seal body 22 also includes an internal shoulder 28 upon which lip seal 26 rests. Lip seal 26 includes a narrow slot 30 which is normally biased to a closed position but may be opened by inserting an instrument from the proximal side. A snap cap 32 may be connected by any conventional means to lip seal body 22 enclosing lip seal 26 therein.

An elastomeric ring 34 is disposed about the proximal portion of snap cap 32 to provide for a snug fit with adapter 36. Adapter 36 may be formed to take any shape necessary depending on the type of equipment to be attached to its proximal end. Here it is shown having an elongated substantially rectangular shape with mating shoulder 38 on its proximal end. Mating shoulder 38 is adapted to make a disengageable, but fluid-tight connection to ribbed seal lower housing 42. The connection is preferably fluid tight to assist in the prevention of insufflation gas leaks, but also disengageable to allow the instrument seal to be removed during a surgical procedure. The removal of the instrument seal from a dual seal system allows for an exchange to be made for a seal more suitable for the upcoming steps of the surgical procedure, or the removal of the instrument seal may simply facilitate the removal irregularly shaped body tissue from the body cavity.

A circular opening 46 is disposed on the proximal end of lower ribbed seal housing 42. Ribbed seal 100 is positioned within the circular opening 46 and enclosed by the connection of upper ribbed seal housing 48 to lower ribbed seal housing 44 by any conventional means. Here snap posts 52 are provided which interface with holes 54 to hold the two housing components together.

Referring now to FIG. 2-5, the ribbed seal 100 of the present invention will be described in greater detail. Ribbed seal 100 is depicted as a septum seal. Septum seals are characterized generally as elastomeric and planar in configuration. Ribbed seal 100 includes two main components. First, is an elastomeric overmold 101 which has a central aperture 102 for the sealed reception of surgical instruments. Overmold portion 101 is substantially flat and extends radially from the aperture. Next, the second main component is a rib array 200 having plurality of individual ribs 201. Rib array 200 and overmold 101 may be composed of the same material, but are more preferably each composed of separate materials selected to have characteristics advantageously affecting the seal performance.

The ribs 201 are preferably formed from a material which will allow them to maintain an axial rigidity while bending easily under a lateral load. A suitable material may be a rigid plastic such as polypropylene which will bend appropriately when configured to have a slender geometry. The overmold portion 101 is preferably formed from a thermoplastic elastomer which will bend and stretch easily upon the insertion of an instrument and will allow the aperture 102 to expand to create a fluid-tight seal around variously sized instruments. If the materials are chosen appropriately, the two components of the ribbed seal 100 may be combined to form a single inseparable unit without adhesives despite having disparate materials. This may be accomplished by using a co-molding or overmolding process. Such a process may involve co-injection wherein the two materials are injected into a mold at about the same time and allowed to set together. Alternatively, an insert molding process can be used where a first material is injected into a mold cavity and allowed to at least partially set, after which the cavity is modified to accommodate the second material. In either case, the materials can be selected such that a strong bond is created between the two materials without the need for an adhesive. Processes other than injection molding may be used to form and combine the components as the particular manufacturing process is not essential to the invention.

Figure 4:
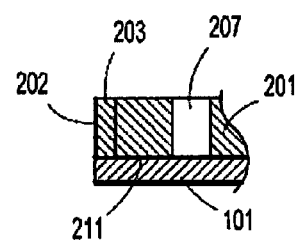
FIG. 4 is an enlarged cross-sectional view of the area of detail B as indicated in FIG. 3 depicting the rib to overmold connection at the outer portions of the ribbed seal.
Figure 3:
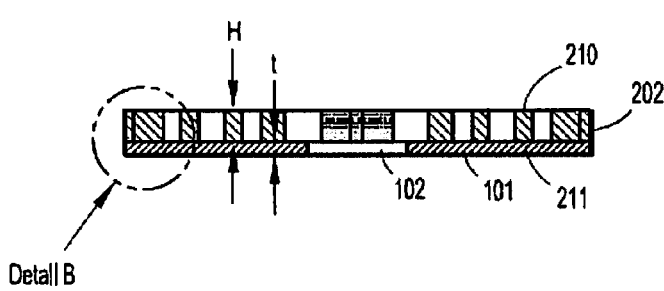
FIG. 3 is a cross-sectional view of the ribbed seal member of FIG. 2 taken along section lines A-A of FIG. 2.
Figure 5:
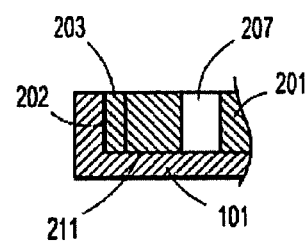
FIG. 5 is a view similar to FIG. 4 depicting an alternate embodiment of the rib to overmold connection of the ribbed seal.

Ribbed seal 100 defines a maximum outer dimension and aperture 102 defines a minimum internal dimension. Ribs 201 are disposed radially about aperture 102. The length L of each rib is its longest dimension which extends radially with respect to ribbed seal 100. Each rib 201 also has a maximum width W and a height H. The width extends in a direction perpendicular to its length and parallel to the overmold 101 while the height extends in a direction perpendicular to both the length and the width. The ribs 201 are connected to one another by outer annular rim 202 around the outer periphery of the array. The annular rim 202 may be molded simultaneously with ribs 201 and from the same material. This will allow the ribs to be connected during manufacturing before the overmold portion 101 is applied to facilitate placement of the rib array into a second mold for application of the overmold portion 101. As depicted in FIG. 4, the overmold 101 may be entirely flat, having a uniform thickness extending to the outer most surface of the annular rim 202. The overmold 101 is attached to the ribs only along their lower face 211. Selecting a relatively rigid material for the annular rim 202 can provide a more rigid structure to the ribbed seal 100. Annular rim 202 may be partially formed from the overmold material as shown in FIG. 5. Such a configuration can provide an outer seal to help prevent the leakage of insufflation gasses around the outer periphery of the circular opening 46 of the lower ribbed seal housing 42. The annular rim 202 may also provide an upper clamping surface 210, best seen in FIG. 6 or 7, which may be positioned to abut upper ribbed seal housing 48 such that ribbed seal 100 is held securely between upper and lower ribbed seal housings 42, 48. The ribs 201 have a secured end 209 adjacent to the annular rim 202 and an opposite free end 208. Ribs 201 also have a lower face 211 adjacent to the overmold 101 and an opposite upper face 210.

Figure 2:
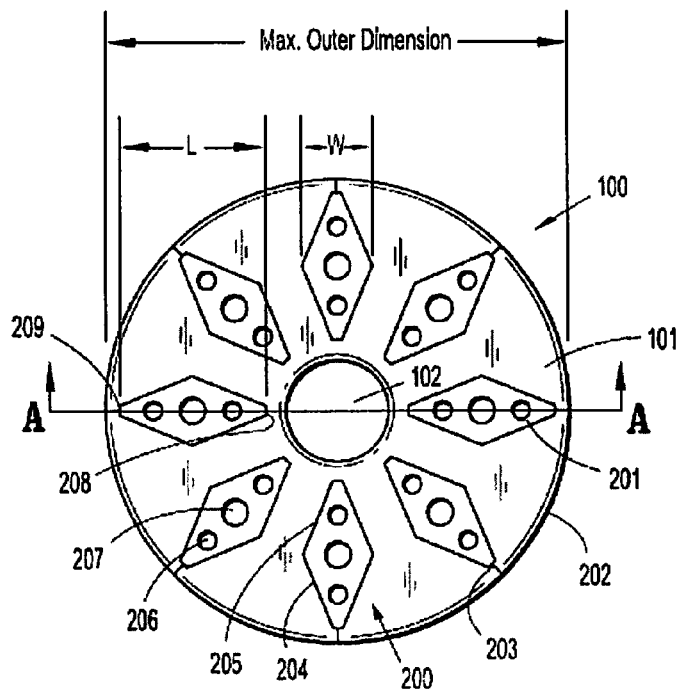
FIG. 2 is a top view of a ribbed seal member.
Figure 6:
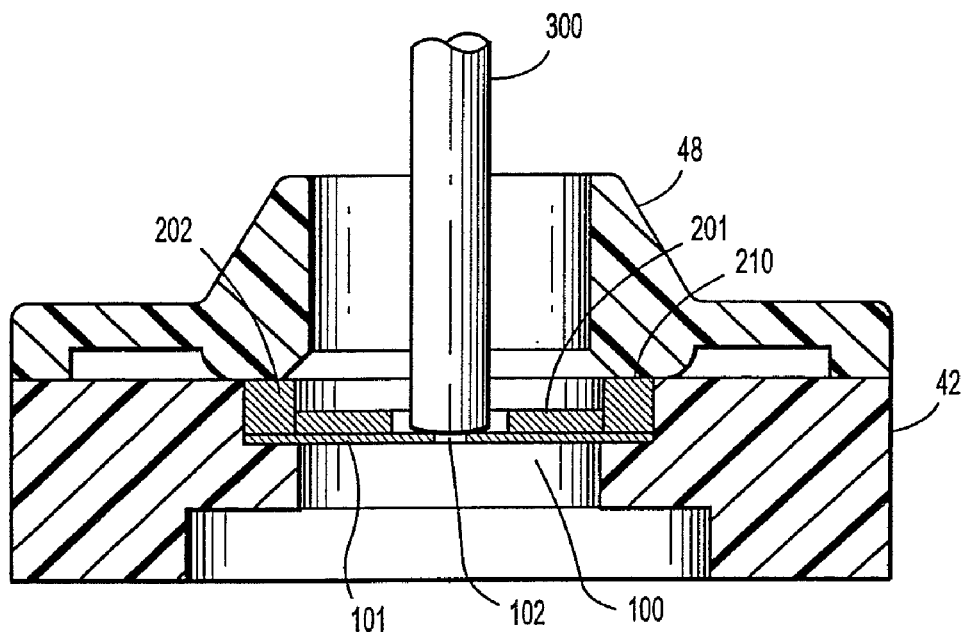
FIG. 6 is a partial cross-sectional view of the upper and lower ribbed seal housings of FIG. 1 containing a ribbed seal and an instrument partially inserted.
Figure 7:
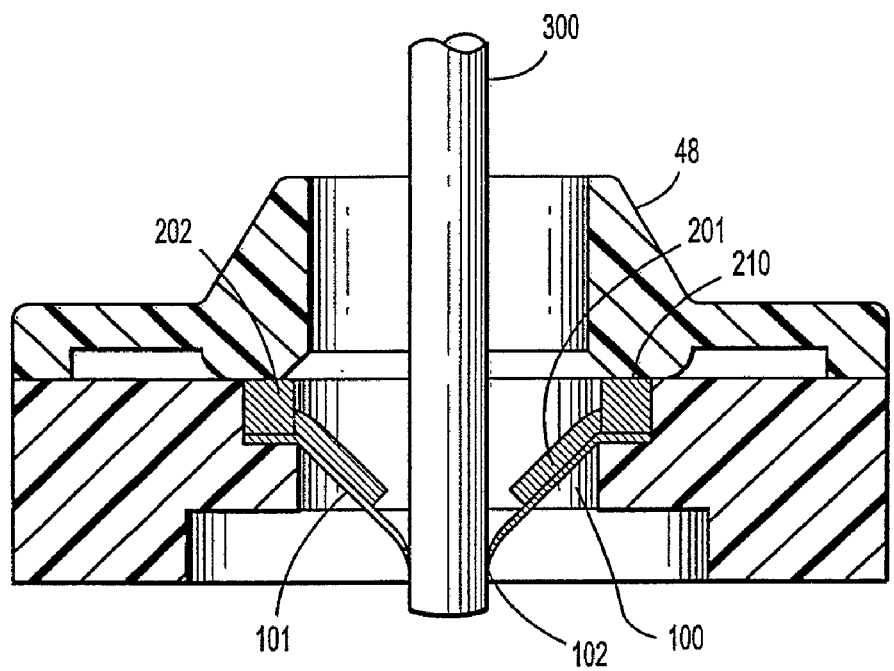
FIG. 7 is a view similar to FIG. 6 depicting a ribbed seal making a fluid-tight connection about an instrument.
Figure 8:
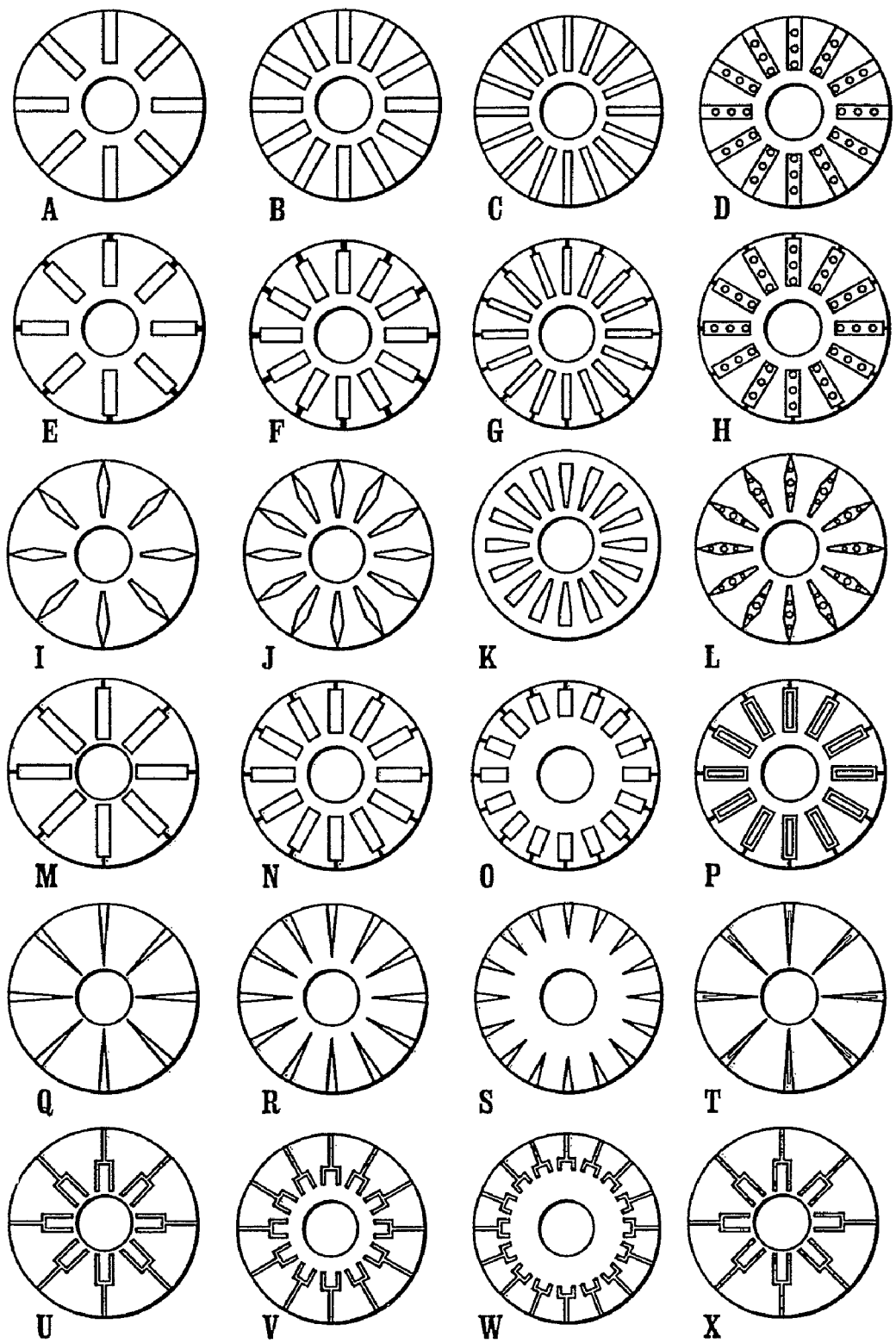
FIG. 8A-8X depict alternate embodiments of the ribbed seal with various rib geometries and rib array configurations.

The geometry of ribs 201 depicted in FIG. 2 is adapted to facilitate the insertion and withdrawal of an instrument from a cannula. Each rib 201 is connected to the annular rim 202 by a reduced profile arm 203 which has a width less than the width of the rib at its secured end 209. Ribs 201 are generally diamond shaped having both an interiorly directed taper 205 and an exteriorly directed taper 204. Also included are central bore 207 and a pair of minor bores 206. Bores 206, 207 may extend through the rib to the lower face 211 as shown, or may terminate at any particular depth. Each of these geometric features is intended to provide stress relief and concentrate bending in certain areas. When an instrument 300 is inserted into the upper seal housing 48, as can be seen in FIG. 6, and the first contact is made with the overmold 101, the ribbed seal 100 is substantially flat. The ribs 201 are therefore initially loaded in a purely lateral direction. Because the ribs are configured to bend easily, the instrument may be inserted without the application of much force. However, when the instrument 300 is ready for removal, the ribbed seal 100 is no longer substantially flat as can be seen in FIG. 7. The ribs 201 will be pivoted distally and the ribbed seal 100 will have assumed a shape approximating a cone to accommodate the instrument 300. In this configuration, when the instrument 300 is withdrawn in a proximal direction there is a significant axial component to the loading of the ribs. Because the ribs are configured to be stiff in buckling to provide radial support for the instrument, ribs will have an inherent tendency to resist the withdrawal of an instrument. The geometry of the rib array as described above can provide strategically located bending zones to ease instrument withdrawal. This may be accomplished by selectively combining any of the geometric features as depicted in FIG. 8.

FIGS. 8A-C demonstrate that the number of ribs in the rib array along with the rib width may be varied to produce a seal member with the desired characteristics for a particular application. A greater number of more slender ribs may bend more easily than fewer but wider ribs while maintaining the necessary radial support characteristics. FIGS. 8E-G depict the use of a reduced profile arm to connect the ribs to the annular rim. This will provide a zone of increased flexibility near the annular rim. FIGS. 8I-K depict the use of an interiorly directed taper to increase flexibility near the aperture. FIGS. I and J also depict the use of exteriorly directed tapers to increase flexibility in regions approaching the annular rim. FIGS. 8M-O depict how the rib length may be varied to provide robust radial support at different diameters within the seal member. The free ends of the ribs define a diameter of increased radial support which may be positioned to accommodate variously sized instruments. FIGS. 8Q-S depict triangularly shaped ribs having only an interiorly directed taper and a full profile connection to the annular rim. FIGS. 8U-W depict ribs having a forked profile with a first leg extending from the annular rim and second and third legs extending from the first leg in a substantially spaced and parallel manner. Finally, FIGS. 8D, H, L, P, T and X depict the use of bores within the ribs to provide zones of increased flexibility.

Although the foregoing disclosure has been described in some detail by way of illustration and example, for purposes of clarity or understanding, it will be obvious that certain changes and modifications may be practiced within the scope of the appended claims.

What is claimed is:

1. A surgical portal apparatus for permitting access to a tissue site, which comprises:
a portal member dimensioned for positioning within body tissue, the portal member having a passageway for providing access to a tissue site and to permit introduction of a surgical object used in performing a surgical procedure adjacent the tissue site; and
a portal seal mounted relative to the portal member and defining a seal axis, the portal seal including a first member comprising an elastomeric material and an inner surface defining a passage to permit passage of the surgical object generally along the seal axis and being adapted to establish a substantial sealed relation with the surgical object, and a second member at least partially embedded within the first member, the second member including an at least partial outer annular element and a plurality of independent ribs indirectly connected to the at least partial outer annular element and extending inwardly toward the seal axis, adjacent independent ribs being in spaced relation and having free ends spaced from the inner surface of the first member, each independent rib being disjoined and free from direct interconnection with the other independent ribs, whereby the ribs are capable of movement during insertion of the surgical object independent of an adjacent rib, the independent ribs dimensioned and arranged to bias the surgical object in general alignment with the seal axis.

2. The surgical portal apparatus according to claim 1 wherein the ribs are adapted to cooperate to bias the surgical object in general alignment with the seal axis.

3. The surgical portal apparatus according to claim 2 wherein the ribs are adapted to articulate relative to the at least partial annular element upon introduction and removal of the surgical object.

4. The surgical portal apparatus according to claim 1 wherein the portal seal is a septum seal defining an aperture, the aperture being the passage.

5. The surgical portal apparatus according to claim 1 wherein the at least one rib includes a tapered segment, the tapered segment defining a width decreasing toward the seal axis.

6. The surgical portal apparatus according to claim 1 wherein the at least one rib includes an intermediate segment and first and second opposed tapered segments extending from the intermediate segment, the first tapered segment defining a width decreasing toward the seal axis, the second segment defining a width decreasing toward the at least partial outer annular element.

7. The surgical portal apparatus according to claim 1 wherein the at least one rib defines an opening therethrough to enhance flexibility of the at least one rib.

8. The surgical portal apparatus according to claim 1 wherein the at least one rib defines a free end adjacent the passage of the first member of the portal seal.

9. The surgical portal apparatus according to claim 8 wherein the free end of the at least one rib is spaced from the passage of the first member of the portal seal.

10. The surgical portal apparatus according to claim 1 wherein the at least one rib includes a first leg connected to the at least partial annular element and second and third legs depending relative to the first leg toward the seal axis.

11. The surgical portal apparatus according to claim 10 wherein the second and third legs are arranged in spaced and generally parallel relation.

12. The surgical portal apparatus according to claim 1 wherein the independent ribs are dimensioned to extend in general orthogonal relation with the seal axis in the absence of a surgical object within the passage of the seal.

13. The surgical portal apparatus according to claim 12 wherein the first member of the seal is substantially flat.

14. The surgical portal apparatus according to claim 1 wherein the ribs of the second member of the seal each comprise a material different from the elastomeric material of the first member of the seal.

15. The surgical portal apparatus of claim 1, wherein at least one of the plurality of independent ribs is indirectly connected to the at least partial outer annular element via an arm.

16. A surgical portal apparatus for permitting access to a tissue site, which comprises:
   a portal member dimensioned for positioning within body tissue, the portal member having a passageway for providing access to a tissue site and to permit introduction of a surgical object used in performing a surgical procedure adjacent the tissue site; and
   a portal seal mounted relative to the portal member and defining a seal axis, the portal seal including a first member comprising an elastomeric material and an inner surface defining an aperture to permit passage of the surgical object generally along the seal axis and being adapted to establish a substantial sealed relation with the surgical object, and a second member at least partially embedded within the first member, the second member including an outer annular element and a plurality of separate and distinct ribs indirectly connected to the outer annular element and extending inwardly toward the seal axis, adjacent ribs being arranged in radial spaced relation and having respective free ends spaced from the inner surface of the first member, each rib being devoid of any direct interconnection with any adjacent ribs whereby the ribs are capable of movement during insertion of the surgical object independent of an adjacent rib.

17. The surgical portal apparatus according to claim 16 wherein the ribs include tapered segments.

18. The surgical portal apparatus according to claim 16 wherein the ribs are dimensioned to extend in general orthogonal relation with the seal axis in the absence of a surgical object within the aperture of the first member of the seal.

19. The surgical portal apparatus according to claim 18 wherein the first member of the seal is substantially planar.

* * * * *